United States Patent [19]

Rawden, Jr.

[11] Patent Number: 5,095,893
[45] Date of Patent: Mar. 17, 1992

[54] FAUCET CONNECTED ORAL CLEANING DEVICE WITH PULSATING FLOW

[76] Inventor: Walter J. Rawden, Jr., 36 W. Redding Rd., Danbury, Conn. 06810

[21] Appl. No.: 690,112

[22] Filed: Apr. 23, 1991

[51] Int. Cl.⁵ .............................................. A61H 9/00
[52] U.S. Cl. ..................................................... 128/66
[58] Field of Search ................................ 128/62 A, 66

[56] References Cited

U.S. PATENT DOCUMENTS

| | | | |
|---|---|---|---|
| 2,595,491 | 5/1952 | Schweikert | 128/62 A |
| 3,568,667 | 3/1971 | Krieger | 128/66 |
| 3,883,074 | 5/1975 | Lambert | 128/66 |
| 3,973,558 | 8/1976 | Stouffer et al. | 128/66 |
| 4,941,459 | 9/1990 | Mathur | 128/66 |

FOREIGN PATENT DOCUMENTS 0097015  12/1983  European Pat. Off. .......... 128/62 A

*Primary Examiner*—John J. Wilson

[57] ABSTRACT

This disclosure is directed to a lavatory or kitchen water faucet with sink or basin whereat the disclosure attaches to the faucet preferably by a quick disconnect coupling means or other attachment means. The attachment means incorporates an aerator valve diverter fitting, the action of which is controlled by movement of a finger operated pull stem that protrudes from the side of said valve diverter fitting. When the stem is pulled, this operation causes the internal valve to divert the water flow which normally passes downwardly through the fitting and into the sink or basin, and instead directs the flow into an axially hollow sleeve or side outlet of the diverter fitting. The aerator valve diverter directs the water flow from the faucet through said side outlet sleeve and into an elongated flexible water flow line. The distal end of said flow line extends to a hand held wand with dual function control valve. The water continues through the valve and discharges into a pulsation mechanism within said hand held wand and finally exits into a water outlet tip, preferably demounted, and preferably able to direct said flow of water for dental cleaning. Moreover, the action of the dual function control valve associated with the wand allows the water flow rate to be adjusted between a maximum and a minimum rate and also allows the water flow to be switched off and on.

4 Claims, 1 Drawing Sheet

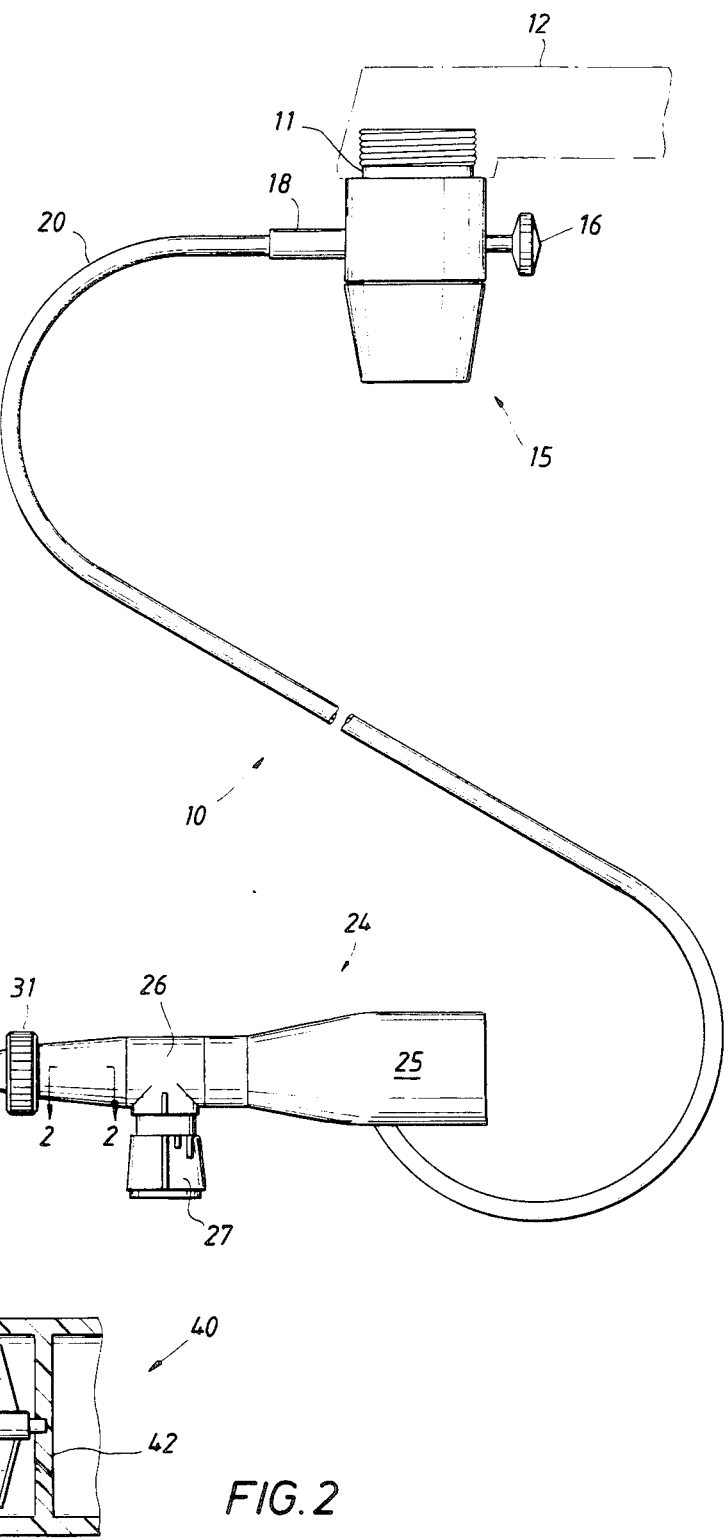

FAUCET CONNECTED ORAL CLEANING DEVICE WITH PULSATING FLOW

BACKGROUND OF THE DISCLOSURE

The present device is an oral cleaning device and more particularly one which uses a flow of water under pressure usually available at a lavatory water faucet. It is a known fact that dental problems are held to a minimum through the use of oral cleaning devices and in particular by the use of those devices being the type that clean the narrow slots between the teeth. In those regions away from the broad surfaces which are otherwise brushed in ordinary dental hygiene, the chance for decay is much greater. Consequently such slots are best cleaned either by the use of dental floss threaded through the slots of the teeth or alternately by direction of a high pressure stream of water through the slots. Commercially available devices provide such pressurized water flow and said devices are intended to clean this region where conventional brushing is not otherwise accessible.

Commercially available devices are known which include an electrically powered pump equipped with a motor normally connected to a 110 VAC power supply by means of an electrical cord. Such devices utilize a pump for pressurizing water where the water is delivered from a storage tank into the pump, and the pump is then operated to deliver the limited water quantity under pressure from the connected tank. The present apparatus is substantially more convenient than the foregoing apparatus and is significantly less costly to manufacture and much less difficult to operate. Rather than using a dedicated pump with its associated motor which requires a separate housing in conjunction with a water storage tank or reservoir, the present approach utilizes an aerator valve diverter fitting which connects directly to a water faucet via a threaded faucet adaptor bushing or other similar means, and a faucet of the type conventionally found at a basin in a bathroom or kitchen. The fitting attaches preferably by threading to the outlet of the faucet. The fitting is equipped with an actuator valve which diverts flow from the faucet through a supply line which extends to a wand. The wand is equipped with a dual purpose control valve for on/off switching plus flow metering. By this construction, a smaller and less costly apparatus is provided.

Moreover, it has longer life in operation by virtue of the reduction in complexity and cost. It is safer in operation in view of the fact that it requires no electrical power. Rather, the power that is required for the operation of this apparatus is furnished by the water supply pressure which is available at the faucet. Because it is connected directly to the faucet and thus the water supply, the present device is continuously furnished with water, thereby eliminating any chance that the apparatus will run out of water. Other commercially available devices deplete their water supply tank when in use and therefore require repetitive refilling of the tank. Since the present disclosure has an infinite source of water, the present disclosure is distinguished over all other devices having a water tank reservoir. The present apparatus can therefore be summarized as a relatively small, even compact construction which is simplified in its operative components to serve as a water jet mechanism finding special use in dental hygiene. The device can be used conveniently at the basin in a bathroom or kitchen. To this end, the present disclosure is provided with an aerator valve diverter fitting which preferably threads to or attaches at the water faucet outlet and is a device which has an actuator valve with stem which selectively allows the water to flow downwardly into the basin whereby the user can first adjust the temperature of the water to a comfortable and selected level and then engage the actuator valve by pulling its stem, whereby the water flow is diverted through the mounted axially hollow tube of the fitting and into a flexible flow line or hose of significant length to thereby permit the user substantial movement at the end of the line. The line extends to a dual function control valve mounted in a wand where the valve is adjustable from full flow to no flow or from a maximum flow rate to a minimum flow rate. This serves as both an on/off valve plus a metering valve. The flow from the valve then emerges from an elongate cleaning tip which is axially hollow and has an outlet opening at the distil end, preferably being bent in the preferred embodiment, and is able to clean readily the teeth of a user and in particular is able to clean the narrow slots and gaps between the teeth where conventional brushing cannot be effectively applied.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 shows the dental hygiene apparatus of the present disclosure mounted on a faucet by means of a threaded bushing which attaches to an aerator valve diverter fitting wherein water flow is diverted into a flexible line or hose which is connected to a hand held wand equipped with an on-off/metering valve, and the water flows through the wand to a demountable cleaning tip having an outlet for directing the water stream as desired;

FIG. 2 shows details of construction of the equipment in the wand; and

FIG. 3 shows details of construction of the connector on the faucet.

DETAILED DESCRIPTION OF THE PREFERRED EMBODIMENT

Attention is first directed to FIG. 1 of the drawings of the present disclosure which shows the equipment generally indicated by the numeral 10 mounted on a faucet 12 shown in phantom line. The faucet 12 is a faucet that is conventionally installed at and above a basin or sink in a bathroom or kitchen. The faucet normally connects with hot and cold water supply lines that are regulated by valves which direct the water through the faucet so that the user may adjust the proportions of the flow and thereby obtain the desired temperature in the flowing water. In any event, the faucet outlet is normally constructed with a set of threads which permit attachment of the present fixture by means of a threaded faucet adaptor bushing 11. Moreover, the aerator valve diverter fitting 15 of the present disclosure is threaded to the bushing 11, and the bushing 11 is in turn threaded to the faucet 12 and can either be installed and removed on every use, or more likely, the fitting 15 can be left permanently on the faucet. In either case, the fitting 15 is a purchased item which is constructed with an axially hollow sleeve 18 which permits water to flow through the sleeve when directed by manipulation of the pull stem 16. The pull stem 16 activates an actuator valve mechanism within the aerator valve diverter fitting which is shifted upon operation of the pull stem. When the stem 16 is pulled, the valve switches and thus diverts the water flow away from the sink and instead through the axially hollow sleeve 18 of the present disclosure. When the stem is reversed or seated, the flow is reversed. When the stem 16 is in its normally static state, the fitting 15 permits the water to flow straight downwardly through the aerator valve diverter fitting 15 so that the faucet operates in the intended and conventional fashion whereby the water flows into the sink or basin. This is the primary water flow path of the faucet. By pulling and thus engaging the pull stem 16, the water is delivered through the lateral hollow outlet sleeve 18 as shown. Otherwise, the water flows directly downwardly vertically through the fitting and into the sink or basin.

When the pull stem 16 is operated, water is diverted through the outlet sleeve 18 and goes into the flexible tubing 20. The tubing 20 has substantial length. While it may not be necessary in every circumstance and condition, typically, about two feet of tubing length is provided. This accommodates all types of installations. Moreover, the line 20 is ideally coiled for nesting in a neat fashion without stringing out over a large area. The line 20 extends to a hand held wand generally indicated at 24. It has a lower handle portion 25. That portion is sized and adapted to fit within the hand of a user. The line 20 extends through the handle portion 25 and connects at the inlet of a valve 26 which is integrally fabricated with the structure of the wand. The valve is provided with a stem that supports an enlargement 27 which is sized for easy finger manipulation. The hand gripped knob 27 can be manipulated to completely close the valve 26 thereby stopping all water flow, or the hand gripped knob 27 can be released to its normally static condition which allows uninterrupted water flow. Rotation of the hand gripped knob 27 adjusts the setting of the valve 26, which is also a metering valve, so that the water flow can be opened and closed from a maximum to a minimum flow rate. The flow is introduced through the line 20, and it is output by the valve 26 through an internal passage which extends to the left as viewed in FIG. 1 of the drawings and is directed to a demountable cleaning tip 30. The tip 30 is grasped by holding the device at a knurled knob 31 and pressing and simultaneously twisting inwardly said knurled knob toward the handle 25 for finger installation of the cleaning tip 30. Moreover, the cleaning tip is an elongated hollow plastic structure of substantial length having a bent tip 32 and a water flow outlet at 33. Water flows out the tip opening 33 as a narrow stream and is directed so that cleaning between teeth can be accomplished.

The cleaning tip 30 is typically used for a dedicated operator. As an advantage, the present apparatus can be used by more than one person, and in that event, each person typically will have their own cleaning tip which is readily installed at the time of cleaning and which is thereafter removed in an easy fashion for storage until the next use. That is accomplished by disconnection of the cleaning tip 30 by grasping the tip at the knurled knob 31 and twisting while simultaneously pulling away from the handle 25 for detachment.

The present apparatus is used in a convenient fashion. In one approach, the fitting 15 is threaded to the faucet 12 via the threaded faucet adaptor bushing 11 and is left indefinitely. Alternately, the fitting 15 can be unthreaded and removed should permanent storage be desired. Since the number of threads associated with the threaded bushing 11 is not excessive, removal or installation can ordinarily be accomplished in less than about one minute merely by unthreading the fitting from or threading the fitting to the faucet 12. Assuming the latter has occurred, the user will typically then operate the water faucet control valves located at the basin (not shown) so that the water flow is adjusted to achieve a desired water temperature. At some point in time, the fitting 15 is then operated to divert water. This operation is achieved rather easily merely by pulling or extending outwardly away from the fitting 15 the protruding finger operated pull stem 16. It is simply operated, thereby diverting the water flow. The water is diverted into the long line 20. There will be a momentary sputter as air in the line 20 is removed. After removal of the air, the water will flow through the equipment of the present disclosure and provide the cleaning services desired.

The water flows through the line 20 to the wand which is typically held in the hand of the user. The water flow is adjusted typically first by directing the tip outlet 33 downwardly toward the basin to avoid splashing, and all the while, the valve 26 is adjusted to a desired metering flow rate by rotation of the hand gripped knob 27. During this adjustment, the valve 26 is adjusted so that the flow rate is then set to carry out dental hygiene by cleaning between the teeth for as long as desired. The valve 26 can be rotated to adjust the flow rate before cleaning, or during cleaning, or after cleaning has ended. Since the wand is in the hand of the user, it is quite possible and conveniently accessible so the user can rotate the knob 27 and thereby adjust the flow rate to an altered flow. The user may also operate the knob 27 at any time in order for the valve 26 to seat and thus close completely, thereby stopping the flow of water altogether. This step is normally performed after a comfortable water temperature has been established and a sufficient flow rate has been set. At this point, it is convenient to stop the water flow altogether in order that no water splashes while directing the tip opening 33 away from the sink or basin and into the mouth of the user. Once the tip opening is properly aimed at the teeth in the user's mouth, the knob 27 can be released which in turn opens the valve 26 to the previously set metered flow rate. When this is accomplished, the user can proceed until cleaning is finished whereupon the water is turned off at the faucet or the user can merely release the pull stem 16 by reversing the direction of movement of the stem. This will then direct the flow of water away from the present apparatus and instead direct the water flow back through the fitting 15 downwardly and into the basin or sink and away from the line 20 because diversion of water flow is no longer necessary.

The present disclosure is intended to provide a relatively inexpensive and safe to use structure. It is ordinarily provided with the necessary components as illustrated so that it is a single assembly which is relatively modest in cost and yet which provides the desirable dental hygiene so otherwise important. To this end, it is preferable that a single fitting be furnished but alternate fitting constructions can be adapted. In part, this is dependent on the nature of the faucet. Since the faucet defines the supporting structure to which the present invention is installed, it may be necessary to change the particular attachment means thereby allowing the aerator valve diverter to connect to the faucet. For instance, the threaded faucet adaptor bushing 11 as illustrated is permitted but the present disclosure also encompasses those fittings which allow attachment by water tight clamping or other connection techniques. The aerator valve diverter fitting in particular directs the flow from the relatively large diameter faucet plumbing fixture conventionally found at basins or sinks into the narrow gauge flexible line. The OD of the flexible line is typically in the range of up to about one quarter inch. Preferably, the tubing is able to accommodate water pressures of about 50 psi or less. Moreover, the water line is typically coiled so that it will nest more readily and be neatly retracted out of the way when not in use. Furthermore, the present apparatus incorporates the hand held wand. The tip 30 can be demounted from the wand. The tip is typically provided in multiple quantities such as furnishing four different tips which are distinguishable, one from another, by some characteristic so that each can be dedicated to an individual user. Multiple tips are normally color coded so that confusion in use does not occur. Moreover, all the components of the present disclosure are furnished from various and sundry sources so they can be readily assembled into the neat and relatively inexpensive assembly making up the disclosed apparatus so that dental hygiene is made available at a reduced cost.

Since the present apparatus is intended for use in a typical apartment, home or other family setting, it is preferable that it be supplied with not one but preferably four or six of the cleaning tips 30. Furthermore, the fitting 15 can be provided with alternate connection means as mentioned above.

FIG. 2 of the drawings shows details of construction of a water pulsation mechanism generally indicated at 40. This is installed within the housing and is preferably located downstream of the valve 26 in the wand shaped handle. It is defined by fixed cylindrical discs fixedly mounted on a common connective stub or shaft therebetween. The upstream front disc 42 is confronted with the water flow after valving elsewhere in the wand. The downstream back disc 48 permits the water to flow out of the mechanism 40 and then to the tip 30. Regarding this pulsation mechanism, it is a passive structure. It is passive in the sense that it derives all power for its operation from the water flow. It is passive in the sense that it requires the dynamic energy of the flowing water to rotate a portion to be described so that the rotating component provides pulsations in the water flow.

The upstream front disc 42 is constructed with ports in it, and the ports are formed at an angle. In other words, they are not merely straight through the disc. Rather, they pass through the front disc 42 at an angle. This angle is common for the several ports. Multiple ports are formed through the front disc 42 at various equally spaced locations and each has a common angle. This converts the water flow which is otherwise straight through the wand handle into a rotating water flow. This rotating water flow is delivered to a free wheeling rotor such that substantial kinetic energy in a spiralling direction results. In other words, the water is rotated on passing through the ports of the front disc 42, and this rotating water catches the free wheeling rotor 41. This rotor 41 is mounted for free wheeling motion around its central hub. The rotor 41 is constructed with a number of radial vanes which extend outwardly from its central hub. The radial vanes intercept the angular water flow to cause rotation of the free wheeling rotor 41. The water surrounds the rotating radial vanes of the rotor 41 and must escape. To this end, the water flow is forced through the fixed back disc 48. The back disc 48 is provided with a number of water outlet holes. The water outlet holes do not need an angular flow component and hence they are formed conveniently straight through the back disc 48. Moreover, the rotor 41 is set into rotation and provides pulsation by blanking off selected areas between vanes. The preferred form of the rotor 41 has an even number of vanes (e.g., 4, or 6) where the spaces or gaps between alternate and adjacent vane pairs are blanked off. This is indicated by the members 50 which parallel the back disc 48 and which are constructed as webbing between the adjacent vanes so that rotation is permitted while the webbing 50 partially and intermittently blanks discharge of water during rotation. At no time does the webbing between adjacent vanes totally cover or blank off all the water outlet holes in the back disc 48. Rather, the webbing only partially interrupts the water flow to create a pulsating effect. The present apparatus is constructed with outlet holes in the back disc 48 at selected locations. The outlet holes are located so that, at any given moment, certain holes are to varying degrees, partially and momentarily blanked off by the webbing 50 as it rotates. This causes the water flow to pulsate. The flow pulsates between a maximum flow rate and a minimum flow rate where the minimum is perhaps between 60% and 85% of the maximum flow rate. Switching the flow completely off is not needed. As will be seen, the webbing 50 comprises an area of a circular disc which is alternated as viewed from the end of the rotor. This therefore comprises a circular disc cumulatively with wedge shaped gaps. If there were 6 vanes defining the rotor, the 6 gaps between vanes would cumulatively define 3 webbing members spaced with 3 similarly shaped gaps.

In summary, this apparatus provides a pulsating water flow which is thought by some to have a special benefit in dental hygiene. Attention is directed to FIG. 3 of the drawings which shows an improved connector with the faucet represented in dotted line. This connector is generally indicated at 60. The connector assembly 60 includes a threaded male aerator nipple 62. This aerator nipple replaces the faucets stock aerator (not shown) and is left permanently at that location. The stock aerator is simply unthreaded from the faucet and the replacement aerator nipple 62 is threaded in its place. Once in place, the aeratore nipple 62 enables attachment of a female snap coupler 63 which in turn supports the diverter/valve structure at 15. The female snap coupler 63 includes an encircling external engagement/disengagement collar 64 which moves by finger manipulation. The external collar 64 can be pulled or otherwise moved axially relative to the fitting 60 so that engagement and disengagement is easily achieved. The snap coupler 63 operates with a set of protruding balls 66 which have the form of small ball bearings or the like which are captured. Preferably there are several balls which are arranged in a circle, and which fit into a recess or groove of the aerator nipple 62 which faces the several ball bearings. The balls 66 thus serve as a detent locking mechanism. A coil spring 68 is included to assure that the snap coupler 63 is held in the latched or locked position.

Accordingly, by finger grip and axial movement of the external collar 64, the balls 66 can be forced into the opposing detent groove to release at which time connection or disconnection is made. One suitable form of equipment thus illustrated in FIG. 3 can be acquired from WPM, Inc. and is known as the model 322 male aerator nipple cooperative with a model 393 female snap coupler. Attached thereto is a model 50-C diverter from National Safety Associates, Inc. the combination of which comprises the connector assembly at 60.

While the foregoing is directed to the preferred embodiment, the scope thereof is defined by the claims which follow.

What is claimed is:

1. Water cleaning apparatus for providing dental hygiene in the gaps between teeth, the apparatus comprising a fitting adapted for connection to a faucet located at a basin or sink wherein the faucet delivers water which is adjustable by a user to a specified temperature while flowing from the faucet, and further wherein said fitting comprises an aerator valve diverter fitting to be fixedly attached to the faucet and said fitting is able to direct a flow of water from the faucet controllably through a side outlet sleeve of the said fitting, and further wherein the fitting is controllably switched by an actuator so that water flows controllably at one of two flow paths, one being water flow downwardly therefrom and the second being flow diverted through said side outlet sleeve of said fitting which sleeve is adapted for connection to an elongate hollow flexible water flow line with said flow line having a specified length to permit a user to operate the apparatus within a specified distance from said faucet, and further wherein the flow line is sized to deliver an adequate water volume to a hand held wand affixed to the distl end of said water flow line wherein water flows through said wand and is directed outwardly therefrom through a detachable tip having a tip opening for directing a narrow water stream therefrom and the tip is an elongated hollow member of sufficient length to extend into the mouth of a user, and wherein said wand permits a user to clean their teeth with water flowing through said wand from said water flow:

a hand operated pull stem actuator valve in said aerator valve diverter fitting which directs water flow into said fitting through said water line:

a dual function control valve in said wand, said control valve includes a valve element and cooperative valve seat for adjustment to provide a metered water flow ranging from a specified maximum flow rate to a specified minimum flow rate:

a quick disconnect coupling connected to said aerator valve diverter which enables connection to the water faucet by said quick disconnect coupling which is removed from or attached to said water faucet thereby allowing the entire apparatus wand to be easily removed from the faucet for storage until the next use:

water pulsation means in said wand:

wherein said water pulsation means includes a rotor within a chamber to receive water flow and said rotor includes vanes intercepting water flow to enable rotation so that said rotor partially and momentarily interrupts water flow to create water flow pulsations: and said wand control valve and said rotor determine water flow rate and rate of pulsations of water flowing from said tip.

2. The cleaning apparatus of claim 1 wherein said control valve includes a moveable stem controlling relative movement of said valve element.

3. Water cleaning for providing dental hygiene in the gaps between teeth, the apparatus comprising:
   (a) a fitting adapted for connection to a faucet located at a basin or sink wherein the faucet delivers water which water flow is adjustable by a user to a specified temperature while flowing from the faucet,
   (b) wherein said fitting comprises an aerator valve diverter fitting releasably attached to the faucet by a quick disconnect means and is able to direct a flow of water from the faucet controllable through a side outlet means of the said fitting,
   (c) an actuator for switching water flow so that water does not flow downwardly therefrom but the water flow is diverted through said side outlet means of the fitting which means is adapted for connection to an elongate hollow flexible water flow line with said flow line having a specified length to permit a user to operate the water cleaning apparatus within a specified distance from said fitting, and further wherein the flow line is sized to deliver an adequate water volume to a hand held wand affixed to the distil end of said water flow line wherein water flows through said wand and is directed outwardly therefrom through a detachable tip having a tip opening for directing a narrow water stream therefrom and said tip is an elongated hollow member of sufficient length to extend into the mouth of a user from said wand,
   (d) wherein said wand permits a user to clean their teeth with water flowing through said wand tip from said water flow line,
   (e) said fitting further comprises a male aerator nipple affixed to the faucet, and also a snap coupler with locking detent means securing a diverter valve structure to said aerator nipple for connection and disconnection, via finger manipulation of an engagement/disengagement collar;
   (f) a hand operated pull stem actuator valve in said aerator valve diverter fitting which directs water flow introduced into said fitting through said water line;
   (g) a dual function control valve having a valve element and cooperative valve seat in said wand, and said control valve includes means for adjustment to provide a metered water flow ranging from a specified maximum flow rate to a specified minimum flow rate;
   (h) water pulsation means in said wand; and
   (i) wherein said water pulsation means includes a rotor within a chamber to receive water flow and said rotor includes vanes intercepting water flow to enable rotation, and said rotating rotor partially and momentarily interrupts water flow to create pulsations.

4. The cleaning apparatus of claim 3 wherein said control valve includes a moveable valve stem controlling relative movement of said valve element.

* * * * *